United States Patent [19]

Jourdan-Laforte

[11] 4,215,058

[45] Jul. 29, 1980

[54] PROCESS OF EPOXIDATION OF OILS

[75] Inventor: Eric Jourdan-Laforte, Ecully, France

[73] Assignee: L'Air Liquide, Societe Anonyme pour l'Etude et l'Exploitation des Brevets Georges Claude, Paris, France

[21] Appl. No.: 937,873

[22] Filed: Aug. 29, 1978

[30] Foreign Application Priority Data

Sep. 13, 1977 [FR] France ................................ 77 27563

[51] Int. Cl.$^2$ ............................................ C07D 301/16

[52] U.S. Cl. ................................ 260/348.27; 106/243; 106/244; 260/348.28

[58] Field of Search ........... 106/243, 244, 250, 18 PF, 106/18 EP; 260/348.23, 348.27, 348.12, 348.28, 45.85 A

[56] References Cited

U.S. PATENT DOCUMENTS

| | | | |
|---|---|---|---|
| 2,667,522 | 1/1954 | McElroy | 260/45.85 A |
| 3,035,000 | 5/1962 | Fullmer | 260/18 PF |
| 3,451,958 | 6/1969 | Riedeman | 260/23 |
| 3,577,556 | 5/1971 | Longoria | 260/45.85 A |

FOREIGN PATENT DOCUMENTS

| | | |
|---|---|---|
| 1184747 | 1/1965 | Fed. Rep. of Germany . |
| 1234770 | 10/1960 | France . |

*Primary Examiner*—Theodore E. Pertilla

*Attorney, Agent, or Firm*—Browdy and Neimark

[57] ABSTRACT

Epoxidation of oil, such as soybean oil, using a peracid, is performed in the presence of a complexing agent for heavy metals selected from nitriloacetic, cyclohexane aminotetracetic and diethylenetriaminopentacetic acids.

7 Claims, No Drawings

PROCESS OF EPOXIDATION OF OILS

FIELD OF INVENTION

The present invention relates to a process of epoxidation of oils, in particular soybean oil, by the action of a peracid.

BACKGROUND OF INVENTION

Epoxidized soybean oil is a product widely used for stabilization of polyvinyl chloride. Mixtures containing this stabilizing agent are used particularly for making packaging materials, such as wrapping film, by extrusion.

To increase the productivity of the extruders, manufacturers of such packaging materials use extruder temperatures as high as possible. It is therefore necessary for the different constituents of the polyvinyl chloride mixture to be stable at these high temperatures.

However, it is known that when epoxidized soybean oil is brought to a high temperature, undesirable decomposition reactions occur followed by condensations and polymerizations reflected by a loss of the oxirane oxygen and a considerable increase in the viscosity of the soil. Thus, PVC compositions containing epoxidized soybean oil are sometimes ruined during high temperature extrusion.

SUMMARY OF INVENTION

A process for epoxidation of oils, in particular soybean oil, has now been found that makes possible the manufacture of products of more constant quality and good heat stability. This improvement in the heat stability of the epoxidized oils is obtained by effecting the epoxidation reaction in the presence of a heavy metal complexing agent.

According to an objective of the invention, the class of complexing agents is selected from particularly nitrilotriacetic, cyclohexanediaminotetracetic and diethylenetriaminopentacetic acids, which leads to very good results, in particular in the form of their alkali or alkaline-earth salts.

In this class of compounds, diethylenetriaminopentacetic acid (DETPA) is preferred as being the product that seems to meets the aims of the invention best, particularly in the sodium salt form, such as trisodium and pentasodium. This compound is particularly valued because of the particular resistance of the chelates that it forms in the hot peroxide baths.

DETAILED DESCRIPTION OF EMBODIMENTS

The amounts of the complexing agent necessary for a good practice of the invention are between 5 and 100 mg per kilogram of soybean oil, preferably between 20 and 40 mg/kg. With diethylenetriaminopentacetic acid in the trisodium salt form used as the complexing agent, the preferential amount is about 30 mg per kilogram of soybean oil.

Epoxidation of the oil is otherwise performed by conventional means of a peracid that is pre-formed or formed in situ. The preferred peracids are lower aliphatic peracids, in particular performic acid. When the peracid is formed in situ, addition of the complexing agent in an aqueous solution of hydrogen peroxide is especially advantageous.

The following specific examples of the invention are offered illustratively:

EXAMPLE 1

(a) Preparation of epoxidized oil

In a cylindrical reactor equipped with an agitator and a double heating and cooling jacket are placed 500 g of refined soybean oil and 25 g of formic acid. To this mixture kept at 60° C. are added over 30 minutes 180 g of $H_2O_2$ at 72% into which have previously been introduced variable amounts of diethylenetriaminopentacetic acid (DETPA) in its trisodium salt form.

After 3 hours reaction at 60° C. there are performed 8 washings, each time with 1600 ml of water and the last traces of water are eliminated by evaporation in a rotary apparatus at 98°-100° C. under a pressure of 17 mm of mercury.

(b) Heat stability test

The oil thus prepared is poured into thin-walled test tubes which are placed in an oven where they are brought to 250° C. for 7 hours.

After this treatment, the viscosity is measured.

The results are given in the following table:

| Concentration of DETPA $Na_3$ | Oxirane number | Iodine number | Viscosity at 30° C. before test (a) | Viscosity at +30° C. after test (b) | $\frac{b-a\%}{a}$ |
|---|---|---|---|---|---|
| 0 mg/kg | 6.72 | 5.6 | 269.5 | 427.1 | 58.5 |
| 10 | 6.75 | 4.7 | 276.1 | 409.5 | 48.3 |
| 20 | 6.75 | 4.8 | 272.9 | 378.7 | 38.8 |
| 30 | 6.83 | 4.9 | 271.4 | 343.9 | 26.7 |
| 40 | 6.73 | 6.0 | 265.8 | 363.4 | 36.7 |

The DETPA $Na_3$ concentrations are expressed in mg/kg of soybean oil.

The oxirane number designates the percentage of oxirane oxygen.

The iodine number expresses the number of grams of iodine able to be fixed per 100 g of oil.

The viscosities at +30° C. before and after test, respectively, a and b, are expressed in centipoises.

It has been found that the best result is obtained when operating in the presence of 30 mg of DETPA $Na_3$ per kilogram of oil.

EXAMPLE 2

Another oil sample is used under the same conditions but with the reaction time extended 30 minutes to lower the residual iodine number; the results are given in the following table which shows the good heat stability of the oil epoxidized in the presence of DETPA $Na_3$.

| Concentration of DETPA $Na_3$ | Oxirane number | Iodine number | Viscosity at 30° C. before test (a) | Viscosity at +30° C. after test (b) | $\frac{b-a\%}{a}$ |
|---|---|---|---|---|---|
| 0 mg/kg | 6.91 | 2.8 | 288.6 | 522.6 | 81.1 |
| 30 mg/kg | 6.88 | 3.4 | 282.5 | 375.3 | 32.8 |

EXAMPLE 3

In a 600-liter reactor equipped with agitation and a double heating and cooling jacket are introduced successively: 300 kg of soybean oil, 20 kg of 80% formic acid by weight, 106 kg of 70% hydrogen peroxide by weight, containing 22.5 g of "VERSENEX 80", a product sold by the Dow Chemical Company, which designates an aqueous solution with 40% active material of the pentasodium salt of diethylenetriaminopentacetic acid.

The hydrogen peroxide is progressively added during a period of 1 to 1.5 hours while the temperature is kept at 60° to 63° C. The reaction is continued for 3 hours at this temperature.

The epoxidized oil is then subjected to 7 successive washings and decantings; 600 liters of water are used for each washing; the temperature is kept between 60° and 70° C. for this washing-decanting phase.

The epoxidized oil is then dried at a temperature between 90°-100° C. under a vacuum made with a water ring pump. To obtain a satisfactory drying of the epoxidized oil, the reactor is kept under vacuum for an hour after the pressure has been lowered to 25 mm of mercury. The epoxidized oil is then cooled between 60°-70° C. and filtered on a filter press equipped with cloths coated with a prelayer of diatomaceous earth.

Heat stability test

The heat stability test is performed according to the mode of operation described in Example 1.

The same lot of soybean oil was epoxidized according to the process described above, by means of hydrogen peroxide with and without VERSENEX 80. The comparative data are given in the following table:

| Concentration of VERSENEX 80 per kg of oil | Oxirane number | Iodine number | Viscosity at 30° C. before test (a) | Viscosity at +30° C. after test (b) | $\frac{b-a\%}{a}$ |
|---|---|---|---|---|---|
| 0 | 6.42 | 2.8 | 286 | 512 | 79 |

-continued

| Concentration of VERSENEX 80 per kg of oil | Oxirane number | Iodine number | Viscosity at 30° C. before test (a) | Viscosity at +30° C. after test (b) | $\frac{b-a\%}{a}$ |
|---|---|---|---|---|---|
| 75 mg | 6.65 | 2.2 | 290 | 395 | 36.2 |

It will be obvious to those skilled in the art that various changes may be made without departing from the scope of the invention and the invention is not to be considered limited to what is described in the specification.

What is claimed is:

1. In a process for the epoxidation of soybean oil by the action of a lower aliphatic peracid, the improvement wherein the epoxidation reaction is performed in the presence of an amount sufficient to improve the stability of the resultant epoxidized soybean oil of a complexing agent, selected from the group consisting of diethylenetriaminopentacetic acid and alkali and alkaline-earth salts thereof, said amount being between 5 and 100 mg per kg of said oil.

2. Process for the epoxidation of oil according to claim 1, wherein the complexing agent is in the form of alkali or alkaline earth salt.

3. Process of epoxidation of oils according to claim 2, wherein the diethylenetriaminopentacetic acid is in the sodium form.

4. Process of epoxidation according to claim 1, wherein the amount of complexing agent used is between 20 and 40 mg/kg of said oil.

5. Process of epoxidation according to claim 3, wherein the diethyltriaminopentacetic acid in the sodium salt form is used in an amount of about 30 mg per kilogram of soybean oil.

6. Process of epoxidation according to claim 1, wherein the peracid is formed in situ by the addition of hydrogen peroxide solution, the complexing agent being added to the hydrogen peroxide solution.

7. Process of epoxidation according to claim 6, wherein the peracid is performic acid.

* * * * *